US 10,883,086 B2

(12) United States Patent
Tripp et al.

(10) Patent No.: US 10,883,086 B2
(45) Date of Patent: Jan. 5, 2021

(54) METHODS AND COMPOSITIONS RELATED TO INCREASED INFLUENZA VIRUS PRODUCTION

(71) Applicant: UNIVERSITY OF GEORGIA RESEARCH FOUNDATION, INC., Athens, GA (US)

(72) Inventors: Ralph A. Tripp, Watkinsville, GA (US); Stephen M. Tompkins, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 90 days.

(21) Appl. No.: 15/742,766

(22) PCT Filed: Jul. 6, 2016

(86) PCT No.: PCT/US2016/041030
§ 371 (c)(1),
(2) Date: Jan. 8, 2018

(87) PCT Pub. No.: WO2017/007784
PCT Pub. Date: Jan. 12, 2017

(65) Prior Publication Data
US 2018/0273908 A1 Sep. 27, 2018

Related U.S. Application Data

(60) Provisional application No. 62/188,817, filed on Jul. 6, 2015, provisional application No. 62/222,243, filed on Sep. 23, 2015.

(51) Int. Cl.
*A61K 39/12* (2006.01)
*C12N 7/00* (2006.01)
*C12N 15/113* (2010.01)
*C12N 5/071* (2010.01)

(52) U.S. Cl.
CPC .............. *C12N 7/00* (2013.01); *A61K 39/12* (2013.01); *C12N 5/0686* (2013.01); *C12N 15/113* (2013.01); *C12N 2310/11* (2013.01); *C12N 2310/14* (2013.01); *C12N 2310/531* (2013.01); *C12N 2760/16134* (2013.01); *C12N 2760/16152* (2013.01)

(58) Field of Classification Search
CPC ..................................................... A61K 39/12
See application file for complete search history.

(56) References Cited

U.S. PATENT DOCUMENTS

| 3,687,808 | A | 8/1972 | Merigan et al. |
| 8,188,060 | B2 | 5/2012 | Khvorova et al. |
| 2009/0280567 | A1 | 11/2009 | Lake et al. |
| 2010/0105100 | A1 | 4/2010 | Sakurada et al. |
| 2012/0009202 | A1 | 1/2012 | Coombs et al. |
| 2012/0192298 | A1 | 7/2012 | Weinstein et al. |
| 2012/0309814 | A1 | 12/2012 | Collard et al. |

FOREIGN PATENT DOCUMENTS

| WO | 2013166264 A2 | 7/2013 |
| WO | WO-2013166264 A2 * | 11/2013 |
| WO | 2014123967 A2 | 8/2014 |

OTHER PUBLICATIONS

Varich, N. L. "The immunosorbtion of influenza virus nucleocapsids from cell lysates as a technique for the studies on viral RNA synthesis." Journal of virological methods, vol. 26, No. 1-2, 1987.
Communication pursuant to Article 94(3) EPC issued in corresponding European application No. 16821887.3, dated Mar. 25, 2020, 6 pages.
Liu et al., "A whole genome screen for HIV restrictions", Retrovirology, Nov. 14, 2011, vol. 8, pp. 1-15.
Meliopoulos et al., "MicroRNA Regulation of Human Protease Genes Essential for Influenza Virus Replication", PloSOne, May 14, 2012, vol. 7(5) e37169, pp. 1-12.
International Search Report issued for Application No. PCT/US2016/041030, dated Sep. 23, 2016.
International Preliminary Report on Patentability issued for Application No. PCT/US2016/041030, dated Jan. 9, 2018.
Extended European Serach Report issued for Application No. 16821887, dated May 2, 2019.
Reversade, B. (2009) Mutations in PYCR1 cause cutis laxa with progeroid features. Nature genetics, vol. 41, No. 9, 1016-1021.
van der Sanden, S M G et al. (2016) Engineering enhanced vaccine cell lines to eradicate vaccine-preventable diseases: the polio end game. J. Viral. vol. 90, No. 4, 1694-1704.
Murray, J. et al. (2017) A universal mammalian vaccine cell line substrate. PLOS ONE, vol. 12, No. 11, e0188333.
Communication Pursuant to Rule 164(1) EPC, issued for Application No. 16821887, dated Jan. 28, 2019.

* cited by examiner

*Primary Examiner* — Thaian N. Ton
*Assistant Examiner* — David A. Montanari
(74) *Attorney, Agent, or Firm* — Meunier Carlin & Curfman LLC

(57) ABSTRACT

Disclosed are compositions and methods for increasing influenza virus production.

8 Claims, 1 Drawing Sheet

METHODS AND COMPOSITIONS RELATED TO INCREASED INFLUENZA VIRUS PRODUCTION

I. BACKGROUND

Vaccines are one of the most important defenses in the fight against infectious disease. Currently, a complex set of factors (population dynamics, bioproduction, costs, etc.) limit the ability to provide adequate immunization coverage worldwide. In particular, bioproduction of vaccines can be expensive and the time required to provide needed quantities of a vaccine can significantly impact the medical benefit to society. This problem is particularly relevant for influenza virus vaccines.

The challenges associated with the U.S. influenza vaccine supply are multi-faceted. Influenza viruses change from year to year, so influenza vaccines must be updated annually to include the viruses that will most likely circulate in the upcoming season. Once the viruses are selected for the new formulation, manufacturers operate under a very tight timeline for producing, testing, releasing and distributing the vaccine. Compounding the problems with the production timeline, the demand for the influenza vaccine varies year to year and even within a given year month to month. If the timing of vaccine production is off, peak demand may not coincide with available supplies.

Due to these time constraints, any problems encountered during production may cause shortages or delays. Additionally, any regulatory delays at even a single production facility can leave supplies critically low and the medical world scrambling to meet demand, and in fact, such problems have impacted the supply in prior influenza seasons.

In 2004, one supplier of influenza vaccine was forced to abandon entire batches of vaccine due to sterility concerns. This shortage highlighted a major problem with current influenza vaccine production. Namely, the vaccine is mass-produced in hen eggs which have to be ordered months in advance to provide the necessary supplies needed. If there is a problem necessitating the production of more vaccine, additional eggs would be need to be ordered which results in further delays before production can even begin. Such delays put even further pressure on the medical community to meet vaccine supply demands. Thus, a new technologies are needed that increase vaccine production at greatly reduced costs.

II. SUMMARY

Disclosed are methods and compositions related to increasing influenza virus production in cells. The disclosed methods and compositions comprise reducing the expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and DUSP19 genes the reduction of which increases influenza viral production.

In one aspect, disclosed herein are cell comprising reduced expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and DUSP19.

In one aspect, disclosed herein are methods of increasing influenza virus production of one or more influenza viruses comprising infecting a cell with an influenza virus; wherein the cell comprises reduced expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and DUSP19 genes.

III. BRIEF DESCRIPTION OF THE DRAWINGS

The accompanying drawings, which are incorporated in and constitute a part of this specification, illustrate several embodiments and together with the description illustrate the disclosed compositions and methods.

IV. DETAILED DESCRIPTION

Figure 1:
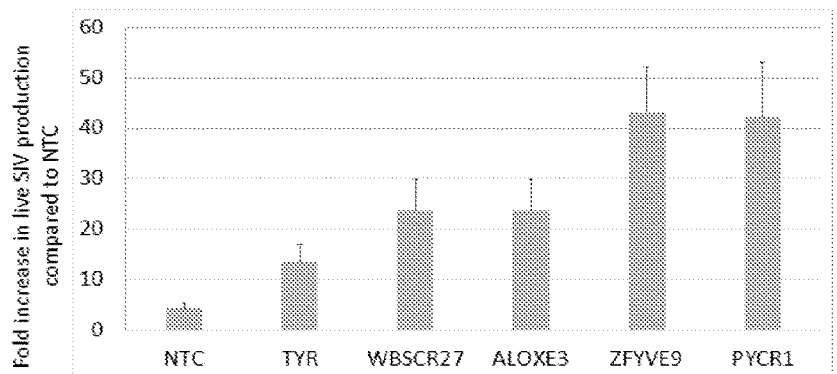
FIG. 1 shows that siRNA-mediated knockdown enhanced live virus production by 10× or greater for all five gene targets identified in the primary screen.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. METHODS OF INCREASING INFLUENZA VIRUS PRODUCTION

Influenza vaccines are used to protect human health and ensure food security. Unfortunately, current manufacturing capabilities are limited and costly, thereby placing significant portions of the human and agricultural animal populations at risk. To address this problem, what are needed are methods of increasing influenza viral titers to enhance viral vaccine production. Accordingly, in one aspect, disclosed herein are methods of increasing influenza virus production of one or more influenza viruses and/or virus strains.

In one aspect, the methods of increasing influenza virus production disclosed herein comprise infecting a cell with an influenza virus; wherein the infected cell comprises reduced expression of at least one gene whose expression represses influenza viral production. For example, disclosed herein, expression of ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 negatively impact influenza viral production. Accordingly, disclosed herein are methods of increasing influenza virus production disclosed herein comprise infecting a cell with an influenza virus; wherein the infected cell comprises reduced expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and DUSP19 genes.

As disclosed herein, the disclosed methods can comprise the reduced expression of any combination of one, two, three, four, five, six, seven, eight, nine, 10, 11, 12, 13, 14, 15, 16, 17, 18, 19, 20, 21, 22, 23, 24, 25, 30, 35, 40, 41, 42, or all 43 of the disclosed genes (i.e., ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, and/or DUSP19). For example, disclosed herein are methods of increasing influenza viral production in a cell or cell line, wherein the cell or cell line comprises reduced expression of PYRC1 alone or in combination with any one, two, three, four, five, six, seven, eight, nine, 10, 11, 12, 13, 14, 15, 16, 17, 18, 19, 20, 21, 22, 23, 24, 25, 30, 35, 40, 41, or 42 other of the selected genes. Thus, for example, in one aspect, disclosed herein are methods of increasing influenza virus production comprising infecting a cell with influenza virus; wherein the cell comprises reduced expression of PYCR1 and one or more ZFYVE9; HD; PLA2G1B; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; ZNF205; DUSP19. In one aspect, the cell or cell lines for use in the disclosed methods of increasing influenza viral production in a cell or cell line can comprise reduced expression of PYCR1 and CNGA4; PYCR1 and ORAI1; PYCR1 and ZFYVE9; PYCR1 and ERCC6; PYCR1 and TYR; PYCR1 and ALOXE3; PYCR1 and B4GALT2; PYCR1 and TRIM4; PYCR1 and WBSCR27; PYCR1 and DUSP19; CNGA4 and ORAI1; CNGA4 and ZFYVE9; CNGA4 and ERCC6; CNGA4 and TYR; CNGA4 and ALOXE3; CNGA4 and B4GALT2; CNGA4 and TRIM4; CNGA4 and WBSCR27; CNGA4 and DUSP19; ORAI1 and ZFYVE9; ORAI1 and ERCC6; ORAI1 and TYR; ORAI1 and ALOXE3; ORAI1 and B4GALT2; ORAI1 and TRIM4; ORAI1 and WBSCR27; ORAI1 and DUSP19; ZFYVE9 and ERCC6; ZFYVE9 and TYR; ZFYVE9 and ALOXE3; ZFYVE9 and B4GALT2; ZFYVE9 and TRIM4; ZFYVE9 and WBSCR27; ZFYVE9 and DUSP19; ERCC6 and TYR; ERCC6 and ALOXE3; ERCC6 and B4GALT2; ERCC6 and TRIM4; ERCC6 and WBSCR27; ERCC6 and DUSP19; TYR and ALOXE3; TYR and B4GALT2; TYR and TRIM4; TYR and WBSCR27; TYR and DUSP19; ALOXE3 and B4GALT2; ALOXE3 and TRIM4; ALOXE3 and WBSCR27; ALOXE3 and DUSP19; B4GALT2 and TRIM4; B4GALT2 and WBSCR27; B4GALT2 and DUSP19; TRIM4 and WBSCR27; TRIM4 and DUSP19; WBSCR27 and DUSP19; PYCR1, CNGA4, and ORAI1; PYCR1, CNGA4, and ZFYVE9; PYCR1, CNGA4, and ERCC6; PYCR1, CNGA4, and TYR; PYCR1, CNGA4, and ALOXE3; PYCR1, CNGA4, and B4GALT2; PYCR1, CNGA4, and TRIM4; PYCR1, CNGA4, and WBSCR27; PYCR1, CNGA4, and DUSP19; PYCR1, ORAI1, and ZFYVE9; PYCR1, ORAI1, and ERCC6; PYCR1, ORAI1, and TYR; PYCR1, ORAI1, and ALOXE3; PYCR1, ORAI1, and B4GALT2; PYCR1, ORAI1, and TRIM4; PYCR1, ORAI1, and WBSCR27; PYCR1, ORAI1, and DUSP19; PYCR1, ZFYVE9, and ERCC6; PYCR1, ZFYVE9, and TYR; PYCR1, ZFYVE9, and ALOXE3; PYCR1, ZFYVE9, and B4GALT2; PYCR1, ZFYVE9, and TRIM4; PYCR1, ZFYVE9, and WBSCR27; PYCR1, ZFYVE9, and DUSP19; PYCR1, ERCC6, and TYR; PYCR1, ERCC6, and ALOXE3; PYCR1, ERCC6, and B4GALT2; PYCR1, ERCC6, and TRIM4; PYCR1, ERCC6, and WBSCR27; PYCR1, ERCC6, and DUSP19; PYCR1; TYR; and ALOXE3; PYCR1; TYR; and B4GALT2; PYCR1; TYR; and TRIM4; PYCR1; TYR; and WBSCR27; PYCR1; TYR; and DUSP19; PYCR1; ALOXE3, and B4GALT2; PYCR1; ALOXE3, and TRIM4; PYCR1; ALOXE3, and WBSCR27; PYCR1, ALOXE3, and DUSP19; PYCR1, B4GALT2, and TRIM4; PYCR1, B4GALT2, and WBSCR27; PYCR1, B4GALT2, and DUSP19; PYCR1, TRIM4, and WBSCR27; PYCR1, TRIM4, and DUSP19; and PYCR1, WBSCR27, and DUSP19.

Also disclosed, for example, are methods of increasing influenza viral production in a cell or cell line, wherein the cell or cell line comprises reduced expression of ZFYVE9 alone or in combination with any one, two, three, four, five, six, seven, eight, nine, or ten other of the selected genes. Thus, in one aspect, disclosed herein are methods of increasing influenza viral production comprising infecting a cell or cell line with influenza virus, wherein the cell or cell line comprises reduced expression of ZFYVE9 and one or more of PYCR1; HD; PLA2G1B; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; BFAR; ZNF205; and DUSP19. In one aspect, the cells for use in the disclosed methods of increasing influenza viral production can comprise reduced expression of ZFYVE9 and CNGA4; ZFYVE9 and ORAI1; ZFYVE9 and PYCR1; ZFYVE9 and ERCC6; ZFYVE9 and TYR; ZFYVE9 and ALOXE3; ZFYVE9 and B4GALT2; ZFYVE9 and TRIM4; ZFYVE9 and WBSCR27; ZFYVE9 and DUSP19; CNGA4 and ORAI1; CNGA4 and PYCR1; CNGA4 and ERCC6; CNGA4 and TYR; CNGA4 and ALOXE3; CNGA4 and B4GALT2; CNGA4 and TRIM4; CNGA4 and WBSCR27; CNGA4 and DUSP19; ORAI1 and PYCR1; ORAI1 and ERCC6; ORAI1 and TYR; ORAI1 and ALOXE3; ORAI1 and B4GALT2; ORAI1 and TRIM4; ORAI1 and WBSCR27; ORAI1 and DUSP19; PYCR1 and ERCC6; PYCR1 and TYR; PYCR1 and ALOXE3; PYCR1 and B4GALT2; PYCR1 and TRIM4; PYCR1 and WBSCR27; PYCR1 and DUSP19; ERCC6 and TYR; ERCC6 and ALOXE3; ERCC6 and B4GALT2; ERCC6 and TRIM4; ERCC6 and WBSCR27; ERCC6 and DUSP19; TYR and ALOXE3; TYR and B4GALT2; TYR and TRIM4; TYR and WBSCR27; TYR and DUSP19; ALOXE3 and B4GALT2; ALOXE3 and TRIM4; ALOXE3 and WBSCR27; ALOXE3 and DUSP19; B4GALT2 and TRIM4; B4GALT2 and WBSCR27; B4GALT2 and DUSP19; TRIM4 and WBSCR27; TRIM4 and DUSP19; WBSCR27 and DUSP19; ZFYVE9, CNGA4, and ORAI1; ZFYVE9, CNGA4, and PYCR1; ZFYVE9, CNGA4, and ERCC6; ZFYVE9, CNGA4, and TYR; ZFYVE9, CNGA4, and ALOXE3; ZFYVE9, CNGA4, and B4GALT2; ZFYVE9, CNGA4, and TRIM4; ZFYVE9, CNGA4, and WBSCR27; ZFYVE9, CNGA4, and DUSP19; ZFYVE9, ORAI1, and PYCR1; ZFYVE9, ORAI1, and ERCC6; ZFYVE9, ORAI1, and TYR; ZFYVE9, ORAI1, and ALOXE3; ZFYVE9, ORAI1, and B4GALT2; ZFYVE9, ORAI1, and TRIM4; ZFYVE9, ORAI1, and WBSCR27; ZFYVE9, ORAI1, and DUSP19; ZFYVE9, PYCR1, and ERCC6; ZFYVE9, PYCR1, and TYR; ZFYVE9, PYCR1, and ALOXE3; ZFYVE9, PYCR1, and B4GALT2; ZFYVE9, PYCR1, and TRIM4; ZFYVE9, PYCR1, and WBSCR27; ZFYVE9, PYCR1, and DUSP19; ZFYVE9, ERCC6, and TYR; ZFYVE9, ERCC6, and ALOXE3; ZFYVE9, ERCC6, and B4GALT2; ZFYVE9, ERCC6, and TRIM4; ZFYVE9, ERCC6, and WBSCR27; ZFYVE9, ERCC6, and DUSP19.

Methods of increasing influenza viral production comprising infecting a cell wherein the cell comprises reduced expression of any other combination of two or more of the disclosed genes ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 is specifically disclosed herein.

As used herein, "increased viral production," "increasing viral production," "increased influenza viral production," and "increasing influenza viral production," refer to a change in viral titers resulting in more virus being produced.

The disclosed methods can be performed with any cell that can be infected with influenza virus. In one aspect, the cells can be of mammalian origin (including, human, simian, porcine, bovine, equine, canine, feline, rodent (e.g., rabbit, rat, mouse, and guinea pig), and non-human primate) or avian including chicken, duck, ostrich, and turkey cells. It is further contemplated that the cell can be a cell of an established mammalian cell line including, but not limited to VERO cells, Madin-Darby Canine Kidney (MDCK) cells, HEp-2 cells, HeLa cells, HEK293 cells, MRC-5 cells, WI-38 cells, EB66, and PER C6 cells.

Influenza Virus is a virus comprising many serotypes, subtypes, and strains known in the art. It is understood and herein contemplated that the disclosed methods can work for any influenza virus including all known Influenza A, Influenza B, and Influenza C viral strains and variants including, but not limited to Influenza A reassortants H1/N1, H1/N2, H1/N3, H1/N4, H1/N5, H1/N6, H1/N7, H1/N8, H1/N9, H1/N10, H2/N11, H2/N1, H2/N2, H2/N3, H2/N4, H2/N5, H2/N6, H2/N7, H2/N8, H2/N9, H2/N10, H2/N11, H3/N1, H3/N2, H3/N3, H3/N4, H3/N5, H3/N6, H3/N7, H3/N8, H3/N9, H3/N10, H3/N11, H4/N1, H4/N2, H4/N3, H4/N4, H4/N5, H4/N6, H4/N7, H4/N8, H4/N9, H4/N10, H4/N11, H5/N1, H5/N2, H5/N3, H5/N4, H5/N5, H5/N6, H5/N7, H5/N8, H5/N9, H5/N10, H5/N11, H6/N1, H6/N2, H6/N3, H6/N4, H6/N5, H6/N6, H6/N7, H6/N8, H6/N9, H6/N10, H6/N11, H7/N1, H7/N2, H7/N3, H7/N4, H7/N5, H7/N6, H7/N7, H7/N8, H7/N9, H7/N10, H7/N11, H8/N1, H8/N2, H8/N3, H8/N4, H8/N5, H8/N6, H8/N7, H8/N8, H8/N9, H8/N10, H8/N11, H9/N1, H9/N2, H9/N3, H9/N4, H9/N5, H9/N6, H9/N7, H9/N8, H9/N9, H9/N10, H9/N11, H10/N1, H10/N2, H10/N3, H10/N4, H10/N5, H10/N6, H10/N7, H10/N8, H10/N9, H10/N10, H10/N11, H11/N1, H11/N2, H11/N3, H11/N4, H11/N5, H11/N6, H11/N7, H11/N8, H11/N9, H11/N10, H11/N11, H12/N1, H12/N2, H12/N3, H12/N4, H12/N5, H12/N6, H12/N7, H12/N8, H12/N9, H12/N10, H12/N11, H13/N1, H13/N2, H13/N3, H13/N4, H13/N5, H13/N6, H13/N7, H13/N8, H13/N9, H13/N10, H13/N11, H14/N1, H14/N2, H14/N3, H14/N4, H14/N5, H14/N6, H14/N7, H14/N8, H14/N9, H14/N10, H14/N11, H15/N1, H15/N2, H15/N3, H15/N4, H15/N5, H15/N6, H15/N7, H15/N8, H15/N9, H15/N10, H15/N11, H16/N1, H16/N2, H16/N3, H16/N4, H16/N5, H16/N6, H16/N7, H16/N8, H16/N9, H16/N10, H16/N11, H17/N1, H17/N2, H17/N3, H17/N4, H17/N5, H17/N6, H17/N7, H17/N8, H17/N9, H17/N10, H17/N11, H18/N1, H18/N2, H18/N3, H18/N4, H18/N5, H18/N6, H18/N7, H18/N8, H18/N9, H18/N10, and H18/N11. It is further understood that the disclosed methods include superinfection (i.e., concurrent infection of multiple viral strains) of a single cell with one, two, three, four, five, six, seven, eight, nine, ten, or more strains, variants, reassortants, or serotypes of influenza virus.

The methods disclosed herein utilize a reduction in expression of a gene or its encoded protein to increase influenza viral production. As used herein "reduced" or "decreased" expression refers to a change in the transcription of a gene, translation of an mRNA, or the activity of a protein encoded by a gene that results in less of the gene, translated mRNA, encoded protein, or protein activity relative to a control. Reduction in expression can be at least a 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the gene expression, mRNA translation, protein expression, or protein activity relative to a control. For example, disclosed herein are methods of increasing influenza virus production disclosed herein comprise infecting a cell with an influenza virus; wherein the infected cell comprises at least 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 genes relative to a control.

It is further understood that one way of referring to a reduction rather than the percentage reduction is as a percentage of the control expression or activity. For example, a cell with at least a 15% reduction in the expression of a particular gene relative to a control would also be a gene with expression that is less than or equal to 85% of the expression of the control. Accordingly, in one aspect are methods wherein the gene expression, mRNA expression, protein expression, or protein activity is less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% of a control. Thus, disclosed herein are methods of increasing influenza virus production disclosed herein comprise infecting a cell with an influenza virus; wherein the infected cell comprises less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% reduction of the expression of at least one gene, mRNA, protein, or protein activity selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 relative to a control. For example, disclosed herein are methods of increasing influenza virus production disclosed herein comprise infecting a cell with an influenza virus; wherein the infected cell comprises less than or equal to 85% reduction of the expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 relative to a control.

It is understood and herein contemplated that the reduced expression can be achieved by any means known in the art including techniques that manipulate genomic DNA, messenger and/or non-coding RNA and/or proteins including but not limited to endogenous or exogenous control elements (e.g., siRNA, shRNA, small molecule inhibitor, and antisense oligonucleotide) and/or mutations are present in or directly target the coding region of the gene, mRNA, or protein or are present in or target a regulator region operably linked to the gene, mRNA, or protein. As such, the technologies or mechanisms that can be employed to modulate a gene of interest include but are not limited to 1) technologies and reagents that target genomic DNA to result in an edited genome (e.g., homologous recombination to introduce a mutation such as a deletion into a gene, zinc finger nucleases, meganucleases, transcription activator-like effectors (e.g., TALENs), triplexes, mediators of epigenetic modification, and CRISPR and rAAV technologies), 2) technologies and reagents that target RNA (e.g. agents that act through the RNAi pathway, antisense technologies, ribozyme technologies), and 3) technologies that target proteins (e.g., small molecules, aptamers, peptides, auxin- or FKBP-mediated destabilizing domains, antibodies).

In one embodiment for targeting DNA, gene modulation is achieved using zinc finger nucleases (ZFNs). Synthetic ZFNs are composed of a custom designed zinc finger binding domain fused with e.g. a FokI DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. Meganucleases, triplexes, CRISPR, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous or exogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5'UTR, the open reading frame, the 3' UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2) lipid-mediated delivery, 3) electroporation, or 4) vector/ plasmid-based expression systems. An introduced RNA molecule may be referred to as an exogenous nucleotide sequence or polynucleotide.

Another gene targeting reagent that uses RNAi pathways includes exogenous small hairpin RNA, also referred to as shRNA. shRNAs delivered to cells via e.g., expression constructs (e.g., plasmids, lentiviruses) have the ability to provide long term gene knockdown in a constitutive or regulated manner, depending upon the type of promoter employed. In one preferred embodiment, the genome of a lentiviral particle is modified to include one or more shRNA expression cassettes that target a gene (or genes) of interest. Such lentiviruses can infect a cell intended for vaccine production, stably integrate their viral genome into the host genome, and express the shRNA(s) in a 1) constitutive, 2) regulated, or (in the case where multiple shRNA are being expressed) constitutive and regulated fashion. In this way, cell lines having enhanced influenza virus production capabilities can be created. It is worth noting, that approaches that use siRNA or shRNA have the added benefit in that they can be designed to target individual variants of a single gene or multiple closely related gene family members. In this way, individual reagents can be used to modulate larger collections of targets having similar or redundant functions or sequence motifs. The skilled person will recognize that lentiviral constructs can also incorporate cloned DNA, or ORF expression constructs.

In another embodiment for modulating gene function, gene suppression can be achieved by large scale transfection of cells with miRNA mimics or miRNA inhibitors introduced into the cells.

In another embodiment, modulation takes place at the protein level. By example, knockdown of gene function at the protein level can be achieved by a number of means including but not limited to targeting the protein with a small molecule, a peptide, an aptamer, destabilizing domains, or other methods that can e.g., down-regulate the activity or enhance the rate of degradation of a gene product. In one preferred instance, a small molecule that binds e.g. an active site and inhibits the function of a target protein can be added to e.g., the cell culture media and thereby introduced into the cell. Alternatively, target protein function can be modulated by introducing e.g., a peptide into a cell that (for instance) prevents protein-protein interactions (see for instance, Shangary et. al., (2009) Annual Review of Pharmacology and Toxicology 49:223). Such peptides can be introduced into a cell by transfection or electroporation, or introduced via an expression construct. Alternatively, peptides can be introduced into cells by 1) adding (e.g., through conjugation) one or more moieties that facilitate cellular delivery, or 2) supercharging molecules to enhance self-delivery (Cronican, J. J. et al (2010) ACS Chem. Biol. 5(8):747-52). Techniques for expressing a peptide include, but are not limited to 1) fusion of the peptide to a scaffold, or 2) attachment of a signal sequence, to stabilize or direct the peptide to a position or compartment of interest, respectively.

It is understood and contemplated herein that some methods of increasing influenza viral production can comprise administering siRNA, miRNA mimics, shRNA, or miRNA inhibitors to the media of an influenza infected cell or cell line to produce a cell or cell line with decreased expression of a gene that inhibits influenza viral production rather than starting the method with a cell or cell line so modified. In one aspect, disclosed herein are method of increasing influenza viral production comprising infecting a cell or cell line with an influenza virus and incubating the cell or cell line under conditions suitable for the production of the virus by the cells, wherein the medium comprises an RNA polynucleotide that inhibits expression of a coding region selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19. Also disclosed are method of increasing influenza virus production wherein the RNA polynucleotide is an siRNA, miRNA mimics, shRNA, or miRNA inhibitor.

In one aspect, it is contemplated herein that any of the disclosed methods of increasing influenza viral production disclosed herein can further comprise incubating the cells or cell line under conditions suitable for the production of the virus by the cells; and harvesting the virus produced by the cells.

In one aspect disclosed herein are methods of increasing influenza virus production comprising infecting any cell or cell line disclosed herein with an influenza virus.

The compositions disclosed herein and the compositions necessary to perform the disclosed methods can be made using any method known to those of skill in the art for that particular reagent or compound unless otherwise specifically noted.

C. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP199 is disclosed and discussed and a number of modifications that can be made to a number of molecules including the ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 are discussed, specifically contemplated is each and every combination and permutation of ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

In one aspect the disclosed compositions can be cells, cell lines, or lysates to be used in the disclosed methods of increasing influenza viral production. In one aspect, disclosed herein are cells or cell lines comprising reduced expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and DUSP19.

As used herein, the term "gene" refers to a transcription unit and regulatory regions that are adjacent (e.g., located upstream and downstream), and operably linked, to the transcription unit. A transcription unit is a series of nucleotides that are transcribed into an RNA molecule. A transcription unit may include a coding region. A "coding region" is a nucleotide sequence that encodes an unprocessed preRNA (i.e., an RNA molecule that includes both exons and introns) that is subsequently processed to an mRNA. A transcription unit may encode a non-coding RNA. A non-coding RNA is an RNA molecule that is not translated into a protein. Examples of non-coding RNAs include microRNA. The boundaries of a transcription unit are generally determined by an initiation site at its 5' end and a transcription terminator at its 3' end. A "regulatory region" is a nucleotide sequence that regulates expression of a transcription unit to which it is operably linked. Nonlimiting examples of regulatory sequences include promoters, enhancers, transcription initiation sites, translation start sites, translation stop sites, transcription terminators, and poly(A) signals. A regulatory region located upstream of a transcription unit may be referred to as a 5' UTR, and a regulatory region located downstream of a transcription unit may be referred to as a 3' UTR. A regulatory region may be transcribed and be part of an unprocessed preRNA. The term "operably linked" refers to a juxtaposition of components such that they are in a relationship permitting them to function in their intended manner. It is understood and herein contemplated that wherein a particular gene is discussed herein, such as, for example, ZFYVE9; HD; PLA2G1B; PYCR1; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; ZNF205, and/or DUSP19; also disclosed are any orthologs and variants of the disclosed gene for use in any composition or method disclosed herein.

As disclosed herein, the disclosed cells, cell lines, or lysates derived therefrom can comprise the reduced expression of any combination of one, two, three, four, five, six, seven, eight, nine, 10, 11, 12, 13, 14, 15, 16, 17, 18, 19, 20, 21, 22, 23, 24, 25, 30, 35, 40, 41, 42, or all 43 of the disclosed genes or a lysate of a cell comprising the same. For example, cells, cell lines, and/or lysates disclosed herein can comprise reduced expression of any one of ZFYVE9; HD; PLA2G1B; PYCR1; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; ZNF205, or DUSP19 in combination with any one or more of ZFYVE9; HD; PLA2G1B; PYCR1; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; ZNF205, and/or DUSP19. For example, the cells, cell lines, and/or lysates can comprise reduced expression of PYRC1 alone or in combination with any one, two, three, four, five, six, seven, eight, nine, or ten other of the selected genes selected from ZFYVE9; HD; PLA2G1B; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; BFAR; ZNF205; and DUSP19. In one aspect, the cells, cell lines, and/or lysates can comprise reduced expression of PYCR1 and CNGA4; PYCR1 and ORAI1; PYCR1 and ZFYVE9; PYCR1 and ERCC6; PYCR1 and TYR; PYCR1 and ALOXE3; PYCR1 and B4GALT2; PYCR1 and TRIM4; PYCR1 and WBSCR27; PYCR1 and DUSP19; CNGA4 and ORAI1; CNGA4 and ZFYVE9; CNGA4 and ERCC6; CNGA4 and TYR; CNGA4 and ALOXE3; CNGA4 and B4GALT2; CNGA4 and TRIM4; CNGA4 and WBSCR27; CNGA4 and DUSP19; ORAI1 and ZFYVE9; ORAI1 and ERCC6; ORAI1 and TYR; ORAI1 and ALOXE3; ORAI1 and B4GALT2; ORAI1 and TRIM4; ORAI1 and WBSCR27; ORAI1 and DUSP19; ZFYVE9 and ERCC6; ZFYVE9 and TYR; ZFYVE9 and ALOXE3; ZFYVE9 and B4GALT2; ZFYVE9 and TRIM4; ZFYVE9 and WBSCR27; ZFYVE9 and DUSP19; ERCC6 and TYR; ERCC6 and ALOXE3; ERCC6 and B4GALT2; ERCC6 and TRIM4; ERCC6 and WBSCR27; ERCC6 and DUSP19; TYR and ALOXE3; TYR and B4GALT2; TYR and TRIM4; TYR and WBSCR27; TYR and DUSP19; ALOXE3 and B4GALT2; ALOXE3 and TRIM4; ALOXE3 and WBSCR27; ALOXE3 and DUSP19; B4GALT2 and TRIM4; B4GALT2 and WBSCR27; B4GALT2 and DUSP19; TRIM4 and WBSCR27; TRIM4 and DUSP19; WBSCR27 and DUSP19; PYCR1, CNGA4, and ORAI1; PYCR1, CNGA4, and ZFYVE9; PYCR1, CNGA4, and ERCC6; PYCR1, CNGA4, and TYR; PYCR1, CNGA4, and ALOXE3; PYCR1, CNGA4, and B4GALT2; PYCR1, CNGA4, and TRIM4; PYCR1, CNGA4, and WBSCR27; PYCR1, CNGA4, and DUSP19; PYCR1, ORAI1, and ZFYVE9; PYCR1, ORAI1, and ERCC6; PYCR1, ORAI1, and TYR; PYCR1, ORAI1, and ALOXE3; PYCR1, ORAI1, and B4GALT2; PYCR1, ORAI1, and TRIM4; PYCR1, ORAI1, and WBSCR27;

PYCR1, ORAI1, and DUSP19; PYCR1, ZFYVE9, and ERCC6; PYCR1, ZFYVE9, and TYR; PYCR1, ZFYVE9, and ALOXE3; PYCR1, ZFYVE9, and B4GALT2; PYCR1, ZFYVE9, and TRIM4; PYCR1, ZFYVE9, and WBSCR27; PYCR1, ZFYVE9, and DUSP19; PYCR1, ERCC6, and TYR; PYCR1, ERCC6, and ALOXE3; PYCR1, ERCC6, and B4GALT2; PYCR1, ERCC6, and TRIM4; PYCR1, ERCC6, and WBSCR27; PYCR1, ERCC6, and DUSP19.

Also disclosed, for example, are cells, cell lines, and/or lysates comprising reduced expression of ZFYVE9 alone or in combination with any one, two, three, four, five, six, seven, eight, nine, or ten other of the selected genes. Thus, in one aspect, disclosed herein are cells, cell lines, and/or lysates comprising reduced expression of ZFYVE9 and one or more of PYCR1; HD; PLA2G1B; EMX2; FGF2; LYK5; RHOBTB2; B4GALT2; ALOXE3; ADAMTS6; BFAR; TRIM4; NRF1; KCNA4; SIM1; SOX10; CYP17A1; GPR155; MAPK8; GPR115; UGT1A3; TYR; FLJ14466; TMPRSS6; TRUB1; GCNT2; RFP2; PRDX6; MVK; MYO7A; ACCN2; CNGA4; WBSCR27; PYGL; STK31; ANXA9; MAK3; RBP4; PCGF1; ERCC6; ORAI1; BFAR; ZNF205; and DUSP19. In one aspect, the cells, cell lines, and/or lysates can comprise reduced expression of ZFYVE9 and CNGA4; ZFYVE9 and ORAI1; ZFYVE9 and PYCR1; ZFYVE9 and ERCC6; ZFYVE9 and TYR; ZFYVE9 and ALOXE3; ZFYVE9 and B4GALT2; ZFYVE9 and TRIM4; ZFYVE9 and WBSCR27; ZFYVE9 and DUSP19; CNGA4 and ORAI1; CNGA4 and PYCR1; CNGA4 and ERCC6; CNGA4 and TYR; CNGA4 and ALOXE3; CNGA4 and B4GALT2; CNGA4 and TRIM4; CNGA4 and WBSCR27; CNGA4 and DUSP19; ORAI1 and PYCR1; ORAI1 and ERCC6; ORAI1 and TYR; ORAI1 and ALOXE3; ORAI1 and B4GALT2; ORAI1 and TRIM4; ORAI1 and WBSCR27; ORAI1 and DUSP19; PYCR1 and ERCC6; PYCR1 and TYR; PYCR1 and ALOXE3; PYCR1 and B4GALT2; PYCR1 and TRIM4; PYCR1 and WBSCR27; PYCR1 and DUSP19; ERCC6 and TYR; ERCC6 and ALOXE3; ERCC6 and B4GALT2; ERCC6 and TRIM4; ERCC6 and WBSCR27; ERCC6 and DUSP19; TYR and ALOXE3; TYR and B4GALT2; TYR and TRIM4; TYR and WBSCR27; TYR and DUSP19; ALOXE3 and B4GALT2; ALOXE3 and TRIM4; ALOXE3 and WBSCR27; ALOXE3 and DUSP19; B4GALT2 and TRIM4; B4GALT2 and WBSCR27; B4GALT2 and DUSP19; TRIM4 and WBSCR27; TRIM4 and DUSP19; WBSCR27 and DUSP19; ZFYVE9, CNGA4, and ORAI1; ZFYVE9, CNGA4, and PYCR1; ZFYVE9, CNGA4, and ERCC6; ZFYVE9, CNGA4, and TYR; ZFYVE9, CNGA4, and ALOXE3; ZFYVE9, CNGA4, and B4GALT2; ZFYVE9, CNGA4, and TRIM4; ZFYVE9, CNGA4, and WBSCR27; ZFYVE9, CNGA4, and DUSP19; ZFYVE9, ORAI1, and PYCR1; ZFYVE9, ORAI1, and ERCC6; ZFYVE9, ORAI1, and TYR; ZFYVE9, ORAI1, and ALOXE3; ZFYVE9, ORAI1, and B4GALT2; ZFYVE9, ORAI1, and TRIM4; ZFYVE9, ORAI1, and WBSCR27; ZFYVE9, ORAI1, and DUSP19; ZFYVE9, PYCR1, and ERCC6; ZFYVE9, PYCR1, and TYR; ZFYVE9, PYCR1, and ALOXE3; ZFYVE9, PYCR1, and B4GALT2; ZFYVE9, PYCR1, and TRIM4; ZFYVE9, PYCR1, and WBSCR27; ZFYVE9, PYCR1, and DUSP19; ZFYVE9, ERCC6, and TYR; ZFYVE9, ERCC6, and ALOXE3; ZFYVE9, ERCC6, and B4GALT2; ZFYVE9, ERCC6, and TRIM4; ZFYVE9, ERCC6, and WBSCR27; ZFYVE9, ERCC6, and DUSP19.

The disclosed cells, cell lines, and lysates derived therefrom can be any cell or cell line that can be stably infected with Influenza virus or a lysate of said infected cells or cell lines. In one aspect, the cells can be of mammalian origin (including, human, simian, porcine, bovine, equine, canine, feline, rodent (e.g., rabbit, rat, mouse, and guinea pig), and non-human primate) or avian including chicken, duck, ostrich, and turkey cells. It is further contemplated that the cell can be a cell of an established mammalian cell line including, but not limited to VERO cells, Madin-Darby Canine Kidney (MDCK) cells, HEp-2 cells, HeLa cells, HEK293 cells, MRC-5 cells, WI-38 cells, EB66, and PER C6 cells. It is further understood that the lysates disclosed herein can be derived from any of the cells or cell lines disclosed herein.

In one aspect, the cells, cell lines, or lysates disclosed herein can have reduced expression of genes, mRNA, or proteins or reduced protein activity that inhibits influenza viral production. Reduction in expression can be at least a 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the gene expression, mRNA translation, protein expression, or protein activity relative to a control. For example, disclosed herein are cells, cell lines, and/or lysates comprising at least 1, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, or 100% reduction of the expression of at least one or more gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 genes relative to a control.

It is further understood that one way of referring to a reduction rather than the percentage reduction is as a percentage of the control expression or activity. For example, a cell with at least a 15% reduction in the expression of a particular gene relative to a control would also be a gene with expression that is less than or equal to 85% of the expression of the control. Accordingly, in one aspect, disclosed herein are cells, cell lines, or lysate wherein the gene expression, mRNA expression, protein expression, or protein activity is less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% of a control. Thus, disclosed herein are cells, cell lines, or lysates comprising less than or equal to 95, 90, 89, 88, 87, 86, 85, 84, 83, 82, 81, 80, 75, 70, 65, 60, 55, 50, 45, 40, 35, 30, 25, 20, 15, 10, 9, 8, 7, 6, 5, 4, 3, 2, 1% reduction of the expression of at least one gene, mRNA, protein, or protein activity selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 relative to a control. For example, disclosed herein are cells, cell lines, and/or lysates comprising less than or equal to 85% reduction of the expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 relative to a control.

It is understood and herein contemplated that the reduced expression can be achieved by any means known in the art including techniques that manipulate genomic DNA, messenger and/or non-coding RNA and/or proteins including but not limited to endogenous or exogenous control elements (e.g., siRNA, shRNA, small molecule inhibitor, and antisense oligonucleotide) and mutations in or directly targeting the coding region of the gene, mRNA, or protein or a control element or mutation in a regulator region operably linked to the gene, mRNA, or protein. As such, the technologies or mechanisms that can be employed to modulate a gene of interest include but are not limited to 1) technologies and reagents that target genomic DNA to result in an edited genome (e.g., homologous recombination to introduce a mutation such as a deletion into a gene, zinc finger nucleases, meganucleases, transcription activator-like effectors (e.g., TALENs), triplexes, mediators of epigenetic modification, and CRISPR and rAAV technologies), 2) technologies and reagents that target RNA (e.g. agents that act through the RNAi pathway, antisense technologies, ribozyme technologies), and 3) technologies that target proteins (e.g., small molecules, aptamers, peptides, auxin- or FKBP-mediated destabilizing domains, antibodies).

In one embodiment for targeting DNA, gene modulation is achieved using zinc finger nucleases (ZFNs). Synthetic ZFNs are composed of a custom designed zinc finger binding domain fused with e.g. a FokI DNA cleavage domain. As these reagents can be designed/engineered for editing the genome of a cell, including, but not limited to, knock out or knock in gene expression, in a wide range of organisms, they are considered one of the standards for developing stable engineered cell lines with desired traits. Meganucleases, triplexes, TALENs, CRISPR, and recombinant adeno-associated viruses have similarly been used for genome engineering in a wide array of cell types and are viable alternatives to ZFNs. The described reagents can be used to target promoters, protein-encoding regions (exons), introns, 5' and 3' UTRs, and more.

Another embodiment for modulating gene function utilizes the cell's endogenous or exogenous RNA interference (RNAi) pathways to target cellular messenger RNA. In this approach, gene targeting reagents include small interfering RNAs (siRNA) as well as microRNAs (miRNA). These reagents can incorporate a wide range of chemical modifications, levels of complementarity to the target transcript of interest, and designs (see U.S. Pat. No. 8,188,060) to enhance stability, cellular delivery, specificity, and functionality. In addition, such reagents can be designed to target diverse regions of a gene (including the 5 'UTR, the open reading frame, the 3' UTR of the mRNA), or (in some cases) the promoter/enhancer regions of the genomic DNA encoding the gene of interest. Gene modulation (e.g., knockdown) can be achieved by introducing (into a cell) a single siRNA or miRNA or multiple siRNAs or miRNAs (i.e., pools) targeting different regions of the same mRNA transcript. Synthetic siRNA/miRNA delivery can be achieved by any number of methods including but not limited to 1) self-delivery (US Patent Application No 2009/0280567A1), 2) lipid-mediated delivery, 3) electroporation, or 4) vector/plasmid-based expression systems. An introduced RNA molecule may be referred to as an exogenous nucleotide sequence or polynucleotide.

Another gene targeting reagent that uses RNAi pathways includes exogenous small hairpin RNA, also referred to as shRNA. shRNAs delivered to cells via e.g., expression constructs (e.g., plasmids, lentiviruses) have the ability to provide long term gene knockdown in a constitutive or regulated manner, depending upon the type of promoter employed. In one preferred embodiment, the genome of a lentiviral particle is modified to include one or more shRNA expression cassettes that target a gene (or genes) of interest. Such lentiviruses can infect a cell intended for vaccine production, stably integrate their viral genome into the host genome, and express the shRNA(s) in a 1) constitutive, 2) regulated, or (in the case where multiple shRNA are being expressed) constitutive and regulated fashion. In this way, cell lines having enhanced influenza virus production capabilities can be created. It is worth noting, that approaches that use siRNA or shRNA have the added benefit in that they can be designed to target individual variants of a single gene or multiple closely related gene family members. In this way, individual reagents can be used to modulate larger collections of targets having similar or redundant functions or sequence motifs. The skilled person will recognize that lentiviral constructs can also incorporate cloned DNA, or ORF expression constructs.

In another embodiment for modulating gene function, gene suppression can be achieved by large scale transfection of cells with miRNA mimics or miRNA inhibitors introduced into the cells.

In another embodiment, modulation takes place at the protein level. By example, knockdown of gene function at the protein level can be achieved by a number of means including but not limited to targeting the protein with a small molecule, a peptide, an aptamer, destabilizing domains, or other methods that can e.g., down-regulate the activity or enhance the rate of degradation of a gene product. In one preferred instance, a small molecule that binds e.g. an active site and inhibits the function of a target protein can be added to e.g., the cell culture media and thereby introduced into the cell. Alternatively, target protein function can be modulated by introducing e.g., a peptide into a cell that (for instance) prevents protein-protein interactions (see for instance, Shangary et. al., (2009) Annual Review of Pharmacology and Toxicology 49:223). Such peptides can be introduced into a cell by transfection or electroporation, or introduced via an expression construct. Alternatively, peptides can be introduced into cells by 1) adding (e.g., through conjugation) one or more moieties that facilitate cellular delivery, or 2) supercharging molecules to enhance self-delivery (Cronican, J. J. et al (2010) ACS Chem. Biol. 5(8):747-52). Techniques for expressing a peptide include, but are not limited to 1) fusion of the peptide to a scaffold, or 2) attachment of a signal sequence, to stabilize or direct the peptide to a position or compartment of interest, respectively.

As discussed above, the compositions and methods disclosed herein fully contemplate cell lines comprising the cells described herein. As used herein, the term "cell line" refers to a clonal population of cells that are able to continue to divide and not undergo senescence. The cell(s) can be derived from any number of sources including mammalian (including but not limited to human, non-human primate, hamster, dog), avian (e.g., chicken, duck), insect, and more. The cell lines contemplated herein can also be modified versions of existing cell lines including but not limited to VERO cells, Madin-Darby Canine Kidney (MDCK) cells, HEp-2 cells, HeLa cells, HEK293 cells, MRC-5 cells, WI-38 cells, EB66, and PER C6 cells. Thus in one aspect disclosed herein are cell lines (including engineered cell lines) comprising a cell; wherein the cell comprises decreased expression of at least one gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 genes relative to a control.

Also disclosed herein are cell lysates derived from the membrane disruption of the cells or cell lines disclosed herein with infected an influenza virus. Cell lysates used to generate vaccines can similarly be derived from any number of cell types and include any cell that is 1) the target for infection by a pathogenic agent (e.g., a virus), 2) used for the production of a virus or a subunit of a vaccine (e.g., an immunogenic protein), and/or 3) used for the production of a biomolecule. Thus, in one aspect disclosed herein are lysates resulting from the disruption of the cell membrane of any influenza virus infected cell or cell line; wherein the cell or cell line comprises reduced expression of at least one or more gene selected from ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 genes relative to a control 1. Nucleic Acids There are a variety of molecules disclosed herein that are nucleic acid based, including for example the nucleic acids that encode, for example ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, and/or DUSP19, or any of the nucleic acids disclosed herein for making ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19 knockouts, knockdowns, variants, mutants, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U or variants thereof. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylaminocarbonyl-oxycholesterol moiety (Crooke et al., *J. Pharmacol. Exp. Ther.*, 1996, 277, 923-937.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules involved in the signaling pathways disclosed herein, for example ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19, or any of the nucleic acids disclosed herein for making ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those of skill in the art understand how to resolve sequence discrepancies and differences and to adjust the compositions and methods relating to a particular sequence to other related sequences. Primers and/or probes can be designed for any given sequence given the information disclosed herein and known in the art.

c) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of any of the disclosed nucleic acids, such as ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19, or the genomic DNA of any of the disclosed nucleic acids, such as ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19, or they can interact with the polypeptide encoded by any of the disclosed nucleic acids, such as ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, FLJ14466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, and/or DUSP19. Often functional nucleic acids are designed to interact with other nucleic acids based on sequence complementarity between the target molecule and the functional nucleic acid molecule. In other situations, the specific recognition between the functional nucleic acid molecule and the target molecule is not based on sequence complementarity between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAse mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline, as well as large molecules, such as reverse transcriptase and thrombin. Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate.

2. Nucleic Acid Delivery

In the methods described above which include the administration and uptake of exogenous DNA or RNA into the cells of a subject or cell (i.e., gene transduction or transfection), the disclosed nucleic acids can be in the form of naked DNA or RNA, or the nucleic acids can be in a vector for delivering the nucleic acids to the cells, whereby the DNA or RNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudo-typed retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

a) Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, include chemical transfectants, or physico-mechanical methods such as electroporation and direct diffusion of DNA. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

b) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus.

Viral vectors are, for example, Adenovirus, Adeno-associated virus, Herpes virus, Lenti virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

c) Retroviral Vectors

A retrovirus is an animal virus belonging to the virus family of Retroviridae, including any types, subfamilies, genus, or tropisms (e.g., Lentivirus). Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

d) Adenoviral Vectors

The construction of replication-defective adenoviruses has been described. The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites. Recombinant adenoviruses achieve gene transduction by binding to specific cell surface receptors, after which the virus is internalized by receptor-mediated endocytosis, in the same manner as wild type or replication-defective adenovirus A viral vector can be one based on an adenovirus which has had the E1 gene removed and these virons are generated in a cell line such as the CHO and HEK293 cell lines. In another preferred embodiment both the E1 and E3 genes are removed from the adenovirus genome.

e) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

f) Large Payload Viral Vectors

Molecular genetic experiments with large human herpes-viruses have provided a means whereby large heterologous DNA fragments can be cloned, propagated and established in cells permissive for infection with herpesviruses. These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

g) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

3. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

In certain embodiments the promoter and/or enhancer region can act as a constitutive promoter and/or enhancer to maximize expression of the region of the transcription unit to be transcribed. Thus, in one embodiment disclosed herein are recombinant cells comprising one or more microRNA and at least one immunoglobulin encoding nucleic acid wherein the expression of the microRNa is constitutive. In such circumstances, the microRNA can be operationally linked to the constitutive promoter. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

In other embodiments, the promoter and/or enhancer region can act as an inducible promoter and/or enhancer to regulate expression of the region of the transcript to be transcribed. The promoter and/or enhancer may be specifically activated either by light, temperature, or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs. Other examples of inducible promoter systems include but are not limited to GAL4 promoter, Lac promoter, Cre recombinase (such as in a cre-lox inducible system), metal-regulated systems such as metallothionein, Flp-FRT recombinase, alcohol dehydrogenase I (alcA) promoter, and steroid regulated systems, such as, estrogen receptor (ER) and glucocorticoid receptor (GR). Inducible systems can also comprise inducible stem loop expression systems. Thus, in one embodiment disclosed herein are recombinant cells comprising one or more microRNA and at least one immunoglobulin encoding nucleic acid wherein the expression of the microRNA is inducible.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA.

The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

4. Sequence Similarities

It is understood that as discussed herein the use of the terms "homology" and "identity" mean the same thing as "similarity." Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

As a first step towards creating enhanced influenza virus vaccine cell lines, the influenza virus-resistance genes in a Vero vaccine cell line were identified using a genome-wide RNAi screen. Validation of the hits demonstrated that modulating host gene expression alone or in combination dramatically increased influenza virus replication by 10- to >100-fold without altering influenza virus antigenicity. Moreover, cell lines containing stable, CRISPR-mediated knockouts of validated genes performed as well or better than cells treated with siRNAs.

To address the need for expanded, low cost, influenza vaccine production, an siRNA genome-wide screen was performed to identify gene modulation events that enhance influenza replication in an influenza virus vaccine line (e.g., VERO cells, MDCK, EB66, and PER C6 cells). Forty-two (43) top scored hits were examined in Madin-Darby Canine Kidney (MDCK) cells for increased influenza virus levels relative to the non-targeting control by ELISA upon gene silencing. Silencing 11 of the 43 genes dramatically increased titers of swine influenza virus (SIV) replication compared to titers in unmodified cells.

Of these 11 genes (PYCR1, CNGA4, ORAI1, ZFYVE9, ERCC6, TYR, ALOXE3, B4GALT2, TRIM4, WBSCR27 and DUSP19), PYCR1, an enzyme that catalyzes the NAD(P)H-dependent conversion of pyroline-5-carboxylate to proline, and ZFYVE9 produce the most significant results.

a) Description of the Technology

To identify host-encoded gene targets that enhanced influenza production, a broad RNAi screen was performed. Details of the experimental procedures are provided: Vero cells in a 96 well format were transfected with siRNA targeting the genes of interest using DharmaFECT 4 (GE Healthcare). After forty-eight hours, cells were infected with influenza virus (WSN (H1N1)) at an MOI of 0.05. Twenty-four hours later, samples were fixed in an acetone: PBS solution. For the ELISA, fixed plates were rehydrated and washed with PBS prior to treatment with a hydrogen peroxide solution to remove endogenous peroxides. Afterwards, plates were washed with PBS and blocked using SuperBlock (Thermo Fisher) containing 4% goat serum (Invitrogen). Following 1-2 hours of blocking, the primary antibody (mouse anti-Nucleoprotein (Biovest International Inc) was added for 1 hour at room temperature, followed by a 0.5% PBST (PBS+Tween 20) wash. The secondary antibody (goat anti-mouse IgG HRP label (Invitrogen) was added for 1 hour, then removed using PBST washes. NeA-Blue substrate (Clinical Sciences) was used for color development following the manufacturer's instructions and the reaction was stopped with 1N HCl. Absorbance was read on a Beckman Coulter Biomek NXp spectrophotometer at 450 nm. Controls used in the experiment included: a non-targeting control siRNA (NTC, GE Healthcare); a positive control siRNA (siATP6VOC, GE Healthcare), a second siRNA (siNP, designed in-house), and a transfection control siRNA (siTOX control, GE Healthcare). In all, ~7,800 genes including those that represented kinase, phosphatase, GPCR, Ion channel, Protease, Ubiquitin, and Drug target libraries (GE Healthcare) were studied.

b) Results

Table 1 below identifies the small list of genes that when down-regulated, significantly enhance influenza production.

Each of these genes can be modulated in a number of ways (e.g., siRNAs, miRNAs, gene editing (e.g. CRISPR, TALEN, ZFN), or by small molecules targeting the respective protein) to increase influenza production in a vaccine manufacturing setting. It is likely that modulation of the gene or protein function enhances influenza production in a number of different cell substrates, including both vaccine manufacturing and non-manufacturing cell types. In addition, it is likely that modulation of the gene or protein function enhances a wide range of influenza strains including but not limited to strains of human, avian, porcine or mixed origins.

TABLE 1

| Z score > 4.0 | | Z score > 3.0 | | Z score > 2.5 | |
|---|---|---|---|---|---|
| ZFYVE9 | 5.6158 | RHOBTB2 | 3.9677 | ANXA9 | 2.98 |
| HD | 4.6645 | B4GALT2 | 3.9677 | MAK3 | 2.9776 |
| PLA2G1B | 4.5443 | ALOXE3 | 3.8798 | RBP4 | 2.9579 |
| PYCR1 | 4.3126 | ADAMTS6 | 3.8621 | PCGF1 | 2.9272 |
| EMX2 | 4.1993 | BFAR | 3.7651 | ERCC6 | 2.9217 |
| FGF2 | 4.1533 | TRI44 | 3.709 | | |
| LYK5 | 4.0763 | NRF1 | 3.7008 | | |
| | | KCNA4 | 3.6603 | | |
| | | SIMI | 3.6242 | | |
| | | SOX10 | 3.5553 | | |
| | | CYP17A1 | 3.5468 | | |
| | | GPR155 | 3.3956 | | |
| | | MAPK8 | 3.3626 | | |
| | | GPR115 | 3.3558 | | |
| | | UGT1A3 | 3.3334 | | |
| | | TYR | 3.329 | | |
| | | FLJ14466 | 3.3191 | | |
| | | TMPRSS6 | 3.3158 | | |
| | | TRUB1 | 3.3146 | | |
| | | GCNT2 | 3.2747 | | |
| | | RFP2 | 3.23 | | |
| | | PRDX6 | 3.1826 | | |
| | | MVK | 3.1777 | | |
| | | MYO7A | 3.1691 | | |
| | | ACCN2 | 3.1596 | | |
| | | CNGA4 | 3.1356 | | |
| | | WBSCR27 | 3.0992 | | |
| | | PYGL | 3.0962 | | |
| | | STK31 | 3.0536 | | |

2. Example 2

The effectiveness of the top gene targets were tested by ELISA using different cell lines and viral strains. Specifically, the effects of siRNA-mediated gene knockdown were tested in the DF-1 chick fibroblast cell line (ATCC CRL-12203) with the WSN (H1N1) strain of influenza (ATCC VR-1520). Simultaneously, ELISA assays were used to assess the effects of gene knockdown on the original swine influenza strain (SIV) in MDCK cells.

As shown in Table 2, knockdown of several genes identified in the primary screen increased WSN production in DF-1 chick fibroblasts as judged by ELISA. Similarly, a subset of the genes identified in the primary screen also enhance the production of swine influenza in MDCK cells.

TABLE 2

| DF1-WSN | | MDCK-SIV | |
|---|---|---|---|
| siRNA | Fold Change vs. NTC | siRNA | Fold change vs. NTC |
| NTC | 1 | NTC | 1 |
| ANXA9 | 1.733831335 | ALOXE3 | 1.548862349 |
| GPR115 | 1.579614704 | B4GALT2 | 1.547903409 |

TABLE 2-continued

| DF1-WSN | | MDCK-SIV | |
|---|---|---|---|
| siRNA | Fold Change vs. NTC | siRNA | Fold change vs. NTC |
| HTT | 1.516905838 | CNGA4 | 1.950658182 |
| PLA2G1B | 1.563751504 | DUSP19 | 1.531688606 |
| PYGL | 1.859477818 | ERCC6 | 1.787812745 |
| RBP4 | 1.93147244 | ORAI1 | 1.834103391 |
| TRUB1 | 1.764275101 | TRIM4 | 1.545590558 |
| PYCR1 | 1.563751504 | PYCR1 | 2.844817555 |
| TYR | 1.753077903 | TYR | 1.554816723 |
| WBSCR27 | 1.612001179 | WBSCR27 | 1.532386017 |
| ZFYVE9 | 1.865474422 | ZFYVE9 | 1.815144211 |

3. Example 3

Figure 2:
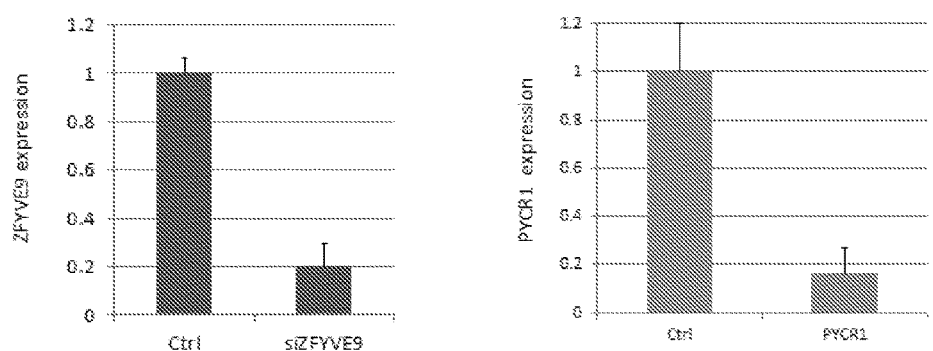
FIG. 2 shows that siRNA-mediated targeting of ZFYVE9 and PYCR1 led to an 80+% decrease in the target transcripts.

Several of the top gene targets identified in the primary screen and validated in DF-1 and MDCK cells were further assessed using an art-recognized TCID50 assay. siRNAs targeting five genes, including TYR, WBSCR27, ALOXE3, ZFYVE9, AND PYCR1, were transfected into MDCK cells to assess the effects of gene knockdown on live swine influenza virus production. The results (FIG. 1) show that siRNA-mediated knockdown enhanced live virus production by 10× or greater for all five gene targets identified in the primary screen. To confirm a correlation between SIV titer increases and gene knockdown, quantitative PCR was performed in MDCK cells transfected with siRNAs targeting the top two hits, ZFYVE9 and PYCR1. The results (FIG. 2) show that siRNA-mediated targeting of ZFYVE9 and PYCR1 led to an 80+% decrease in the target transcripts. Thus, there is a strong correlation between target transcript knockdown and an increase in SIV live virus production.

What is claimed is:

1. An in vitro method of increasing influenza virus production of one or more influenza viruses comprising infecting a cell with an influenza virus; wherein the cell comprises reduced expression of at least one gene selected from HD, PLA2G1B, PYCR1, EMX2, FGF2, RHOBTB2, B4GALT2, ALOXE3, ADAMTS6, TRIM4, NRF1, SIM1, SOX10, CYP17A1, GPR155, GPR115, UGT1A3, TYR, F1114466, TMPRSS6, TRUB1, GCNT2, RFP2, PRDX6, MYO7A, ACCN2, CNGA4, WBSCR27, PYGL, ANXA9, MAK3, RBP4, PCGF1, ERCC6, ORAI1, ZNF205, and DUSP19 genes.

2. The method of claim 1, wherein the cell comprises reduced expression of PYCR1.

3. The method of claim 2, wherein the cell being infected with influenza virus further comprises reduced expression of ZFYVE9, HD, PLA2G1B, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, F1114466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, or DUSP19.

4. The method of claim 1, wherein the reduction occurs through a mutation in a regulator region operably linked to the coding region for HD, PLA2G1B, PYCR1, EMX2, FGF2, RHOBTB2, B4GALT2, ALOXE3, ADAMTS6, TRIM4, NRF1, SIM1, SOX10, CYP17A1, GPR155, GPR115, UGT1A3, TYR, F1114466, TMPRSS6, TRUB1, GCNT2, RFP2, PRDX6, MYO7A, ACCN2, CNGA4, WBSCR27, PYGL, ANXA9, MAK3, RBP4, PCGF1, ERCC6, ORAI1, ZNF205, or DUSP19 genes.

5. The method of claim 1, wherein the reduction in gene expression occurs through an exogenous control element.

6. The method of claim 5, wherein the exogenous control element targets the coding region for one or more of ZFYVE9, HD, PLA2G1B, PYCR1, EMX2, FGF2, LYK5, RHOBTB2, B4GALT2, ALOXE3, ADAMTS6, BFAR, TRIM4, NRF1, KCNA4, SIM1, SOX10, CYP17A1, GPR155, MAPK8, GPR115, UGT1A3, TYR, F1114466, TMPRSS6, TRUB1, GCNT2, RFP2, PRDX6, MVK, MYO7A, ACCN2, CNGA4, WBSCR27, PYGL, STK31, ANXA9, MAK3, RBP4, PCGF1, ERCC6, ORAI1, ZNF205, or DUSP19 genes.

7. The method of claim 1, wherein the reduction of gene expression occurs through insertion, substitution, or deletion of a portion of the coding region using a nuclease selected from the group consisting of zinc finger nucleases (ZFNs), meganucleases, transcription activator-like effector nucleases (TALENs), triplexes, mediators of epigenetic modification, CRISPR and rAAV.

8. The method of claim 1, wherein the influenza virus is selected from at least one strain of Influenza A virus, Influenza B virus, or Influenza C virus.

* * * * *